(12) United States Patent
Vaillancourt et al.

(10) Patent No.: US 8,066,678 B2
(45) Date of Patent: Nov. 29, 2011

(54) SAFETY NEEDLE WITH COLLAPSIBLE SHEATH

(75) Inventors: Vincent L. Vaillancourt, Livingston, NJ (US); Michael J. Vaillancourt, Chester, NJ (US)

(73) Assignee: Bard Access Systems, Inc., Salt Lake City, UT (US)

( * ) Notice: Subject to any disclaimer, the term of this patent is extended or adjusted under 35 U.S.C. 154(b) by 2086 days.

(21) Appl. No.: 10/320,168

(22) Filed: Dec. 16, 2002

(65) Prior Publication Data

US 2003/0114797 A1   Jun. 19, 2003

Related U.S. Application Data

(60) Provisional application No. 60/339,786, filed on Dec. 17, 2001.

(51) Int. Cl.
*A61M 5/32* (2006.01)
(52) U.S. Cl. .................................. 604/198; 604/192
(58) Field of Classification Search .................. 604/263, 604/187, 192, 198, 110, 162, 164.01, 164.07, 604/264, 533; 128/919
See application file for complete search history.

(56) References Cited

U.S. PATENT DOCUMENTS

| | | | |
|---|---|---|---|
| 2,847,995 A | 8/1958 | Adams | |
| 2,876,770 A | 3/1959 | White | |
| 2,925,083 A | 2/1960 | Craig | |
| 3,134,380 A | 5/1964 | Armao | |
| 3,306,290 A | 2/1967 | Weltman | |
| 4,160,450 A | 7/1979 | Doherty | |
| 4,564,054 A * | 1/1986 | Gustavsson | 141/329 |
| 4,592,744 A | 6/1986 | Jagger et al. | |
| 4,632,671 A | 12/1986 | Dalton | |
| 4,645,494 A | 2/1987 | Lee et al. | |
| 4,645,495 A | 2/1987 | Vaillancourt | |
| 4,725,267 A | 2/1988 | Vaillancourt | |
| 4,760,847 A | 8/1988 | Vaillancourt | |
| 4,813,939 A | 3/1989 | Marcus | |
| 4,846,809 A | 7/1989 | Sims | |

(Continued)

FOREIGN PATENT DOCUMENTS

DE   3808688 A1   1/1989

(Continued)

OTHER PUBLICATIONS

EP 03257490 filed Nov. 27, 2003 Office Action dated Aug. 9, 2007.

(Continued)

*Primary Examiner* — Christopher D Koharski
(74) *Attorney, Agent, or Firm* — Rutan & Tucker, LLP

(57) ABSTRACT

The needle of a syringe, wire guide, biopsy needle, Huber needle and the like is drawn into a protective cap and sheath arrangement after use for disposal purposes. The cap is tethered to a housing in which the needle is mounted by the sheath. The sheath is made of a film material that has a high tensile strength and a low percent of elongation, such as polyester. The sheath is initially mounted about the needle in a collapsed accordion-like condition between the cap and housing. When the cap is moved along the needle, the sheath is played out over the needle. The cap houses a spring clip to snap over the bore through which the needle is retracted to prevent re-emergence of the needle. The flexible nature of the sheath allows the sheath to pass about the two legs of the Huber needle.

13 Claims, 13 Drawing Sheets

U.S. PATENT DOCUMENTS

| | | | |
|---|---|---|---|
| 5,013,305 A | 5/1991 | Opie et al. | |
| 5,053,017 A | 10/1991 | Chamuel | |
| 5,092,852 A | 3/1992 | Poling | |
| 5,176,655 A | 1/1993 | McCormick | |
| 5,295,972 A | 3/1994 | Mischenko | |
| 5,312,371 A | 5/1994 | Dombrowski | |
| 5,334,158 A | 8/1994 | McLees | |
| 5,336,187 A * | 8/1994 | Terry et al. | 604/110 |
| 5,419,766 A | 5/1995 | Chang et al. | |
| 5,487,728 A | 1/1996 | Vaillancourt | |
| 5,487,733 A | 1/1996 | Caizza | |
| 5,490,841 A | 2/1996 | Landis | |
| 5,531,713 A | 7/1996 | Mastronardi et al. | |
| 5,575,773 A | 11/1996 | Song et al. | |
| 5,584,818 A | 12/1996 | Morrison | |
| 5,685,860 A * | 11/1997 | Chang et al. | 604/192 |
| 5,695,474 A | 12/1997 | Daugherty | |
| 5,817,070 A | 10/1998 | Tamaro | |
| 5,853,393 A | 12/1998 | Bogert | |
| 5,858,004 A | 1/1999 | Shields | |
| 5,885,255 A | 3/1999 | Jaeger | |
| 6,042,570 A | 3/2000 | Bell et al. | |
| 6,238,375 B1 | 5/2001 | Powell | |
| 6,497,669 B1 | 12/2002 | Kensey | |
| 6,500,155 B2 | 12/2002 | Sasso | |
| 6,623,462 B2 | 9/2003 | Guzzo et al. | |
| 6,629,959 B2 | 10/2003 | Kuracina et al. | |
| 6,659,984 B2 | 12/2003 | Maclean Crawford et al. | |
| 6,689,102 B2 | 2/2004 | Greene | |
| 6,699,217 B2 | 3/2004 | Bennett et al. | |
| 6,719,727 B2 | 4/2004 | Brimhall et al. | |
| 6,749,588 B1 | 6/2004 | Howell et al. | |
| 6,808,509 B1 | 10/2004 | Davey | |
| 6,824,530 B2 | 11/2004 | Wagner et al. | |
| 6,932,803 B2 | 8/2005 | Newby | |
| 6,969,372 B1 | 11/2005 | Halseth | |
| 6,972,002 B2 | 12/2005 | Thorne | |
| 7,147,623 B2 | 12/2006 | Mathiasen | |
| 7,150,725 B2 | 12/2006 | Wilkinson | |
| 7,214,208 B2 | 5/2007 | Vaillancourt et al. | |
| 7,361,159 B2 | 4/2008 | Fiser et al. | |
| 7,407,493 B2 | 8/2008 | Cane' | |
| 7,438,703 B2 | 10/2008 | Barrus et al. | |
| 7,601,139 B2 | 10/2009 | Woehr et al. | |
| 7,604,616 B2 | 10/2009 | Thoresen et al. | |
| 7,637,893 B2 | 12/2009 | Christensen et al. | |
| 7,717,888 B2 | 5/2010 | Vaillancourt et al. | |
| 2001/0039401 A1 | 11/2001 | Ferguson et al. | |
| 2002/0055711 A1 | 5/2002 | Lavi et al. | |
| 2002/0099340 A1 | 7/2002 | Crawford et al. | |
| 2002/0151852 A1 | 10/2002 | Crawford et al. | |
| 2002/0165497 A1 | 11/2002 | Greene | |
| 2002/0177816 A1 | 11/2002 | Brimhall et al. | |
| 2002/0177818 A1 | 11/2002 | Vaillancourt | |
| 2002/0183652 A1 | 12/2002 | Kensey | |
| 2003/0093101 A1 | 5/2003 | O'Heeron et al. | |
| 2003/0105430 A1 | 6/2003 | Lavi et al. | |
| 2003/0114797 A1 | 6/2003 | Vaillancourt et al. | |
| 2003/0144627 A1 | 7/2003 | Woehr et al. | |
| 2003/0181872 A1 | 9/2003 | Newby | |
| 2003/0199827 A1 | 10/2003 | Thorne | |
| 2004/0044318 A1 | 3/2004 | Fiser et al. | |
| 2004/0049159 A1 | 3/2004 | Barrus et al. | |
| 2004/0236288 A1 | 11/2004 | Howell et al. | |
| 2005/0027263 A1 | 2/2005 | Woehr et al. | |
| 2005/0090784 A1 | 4/2005 | Nielsen et al. | |
| 2005/0107743 A1 | 5/2005 | Fangrow | |
| 2005/0124938 A1 | 6/2005 | Yang | |
| 2005/0137528 A1 | 6/2005 | Wilkinson | |
| 2006/0155245 A1 | 7/2006 | Woehr | |
| 2006/0161116 A1 | 7/2006 | Willis et al. | |
| 2007/0038182 A1 | 2/2007 | Bialecki et al. | |
| 2007/0038183 A1 | 2/2007 | Bialecki et al. | |
| 2007/0038184 A1 | 2/2007 | Bialecki et al. | |
| 2007/0038185 A1 | 2/2007 | Albert et al. | |
| 2007/0073221 A1 | 3/2007 | Bialecki et al. | |
| 2007/0073222 A1 | 3/2007 | Lilley et al. | |
| 2008/0147003 A1 | 6/2008 | Menzi et al. | |
| 2008/0262434 A1 | 10/2008 | Vaillancourt | |
| 2009/0005743 A1 | 1/2009 | Vaillancourt et al. | |
| 2009/0254050 A1 | 10/2009 | Bottcher | |
| 2009/0281499 A1 | 11/2009 | Harding et al. | |

FOREIGN PATENT DOCUMENTS

| | | |
|---|---|---|
| DE | 3802353 A1 | 8/1989 |
| DE | 20210394 U1 | 9/2002 |
| DE | 20210394 U1 | 9/2002 |
| EP | 451040 A1 | 10/1991 |
| EP | 0747082 | 12/1996 |
| EP | 0747082 A2 | 12/1996 |
| EP | 0763369 A1 | 3/1997 |
| EP | 1430921 A2 | 6/2004 |
| FR | 2684006 A1 | 5/1993 |
| JP | 61-25558 A | 5/1994 |
| JP | 6226919 A | 8/1994 |
| JP | 7-148270 A | 6/1995 |
| JP | 9099071 A | 4/1997 |
| JP | 2002345955 A | 12/2002 |
| JP | 4355567 | 8/2009 |
| WO | 9400172 A1 | 1/1994 |
| WO | 9806642 | 2/1998 |

OTHER PUBLICATIONS

EP 03257490 filed Nov. 27, 2003 Search Report dated Jul. 23, 2004.
JP 2003-416415 filed Dec. 15, 2003 Office Action dated Feb. 23, 2007.
JP 2003-416415 filed Dec. 15, 2003 Office Action dated May 30, 2006.
U.S. Appl. No. 11/788,542, filed Apr. 20, 2007 Final Office Action dated Dec. 16, 2009.
U.S. Appl. No. 11/788,542, filed Apr. 20, 2007 Non-Final Office Action dated Aug. 27, 2008.
U.S. Appl. No. 11/788,542, filed Apr. 20, 2007 Non-Final Office Action dated Jan. 8, 2009.
U.S. Appl. No. 11/788,542, filed Apr. 20, 2007 Non-Final Office Action dated Jul. 10, 2009.
U.S. Appl. No. 12/221,034, filed Jul. 30, 2008 Final Office Action dated Dec. 8, 2009.
U.S. Appl. No. 12/221,034, filed Jul. 30, 2008 Non-Final Office Action dated Jan. 30, 2009.
U.S. Appl. No. 12/221,034, filed Jul. 30, 2008 Non-Final Office Action dated Jun. 26, 2009.
U.S. Appl. No. 12/221,034, filed Jul. 30, 2008 Notice of Allowance dated Feb. 25, 2010.

* cited by examiner

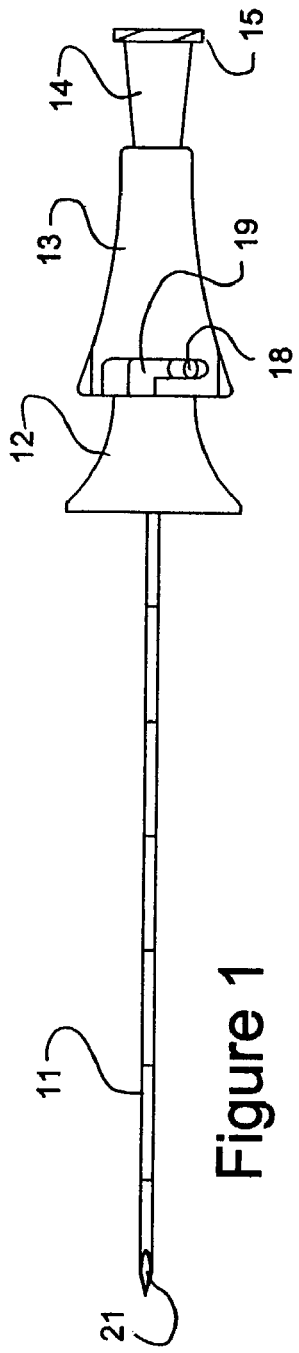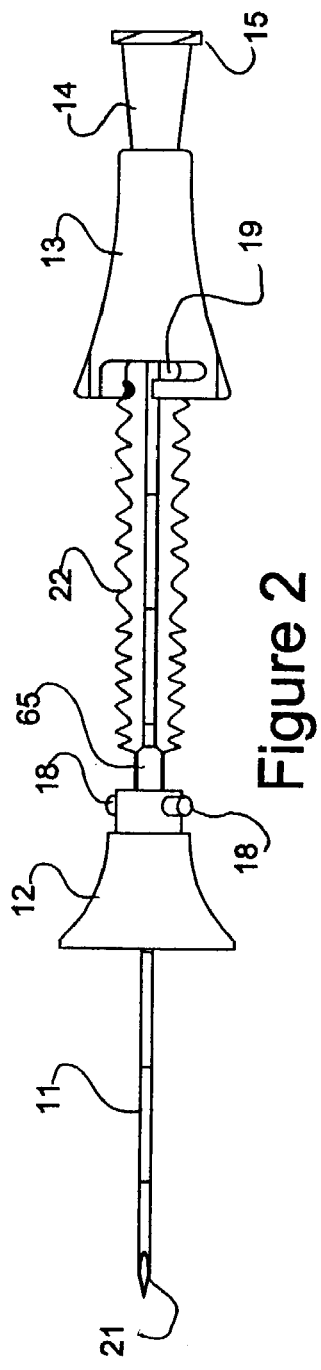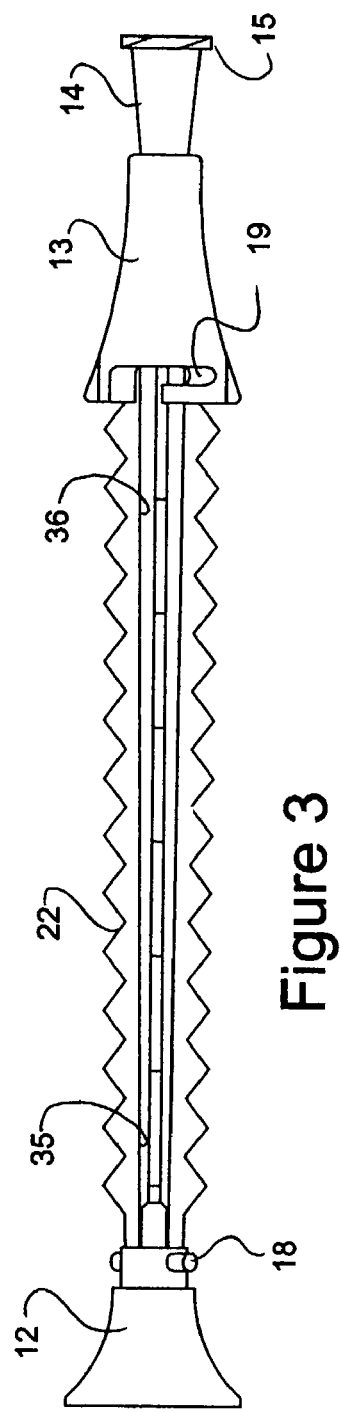

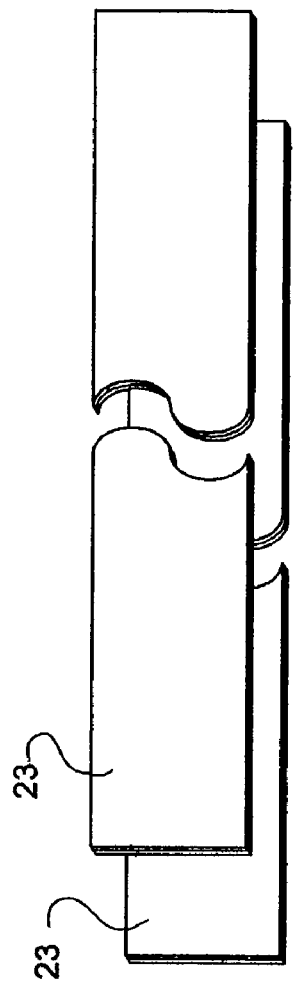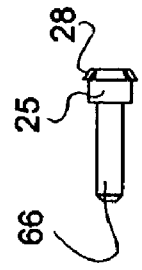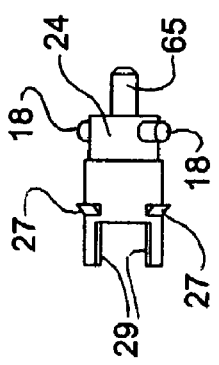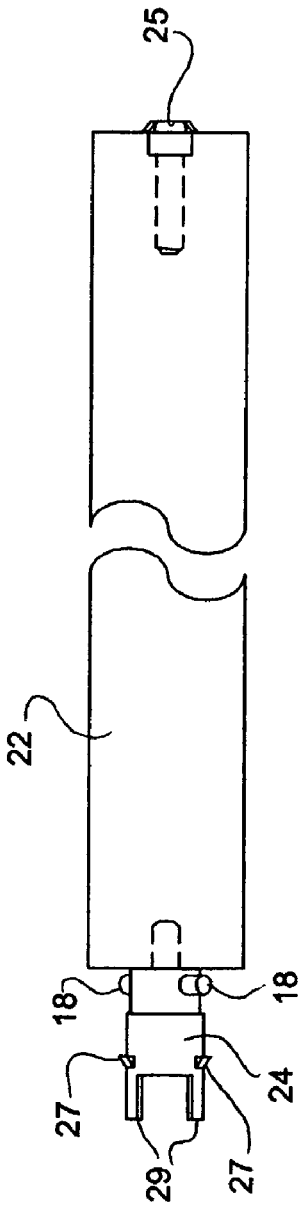

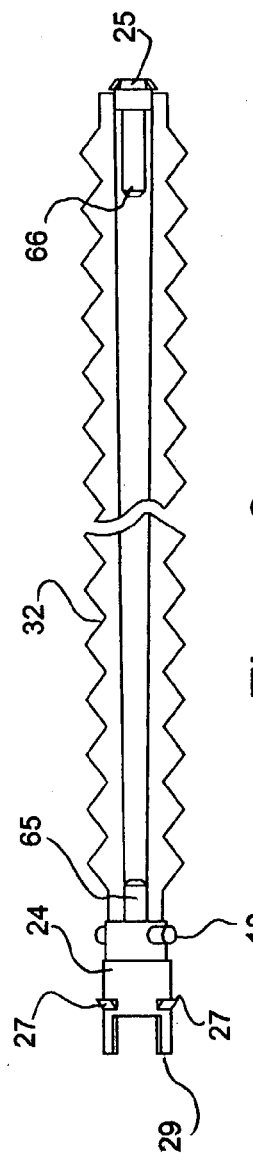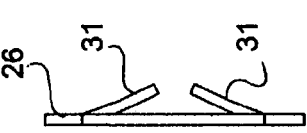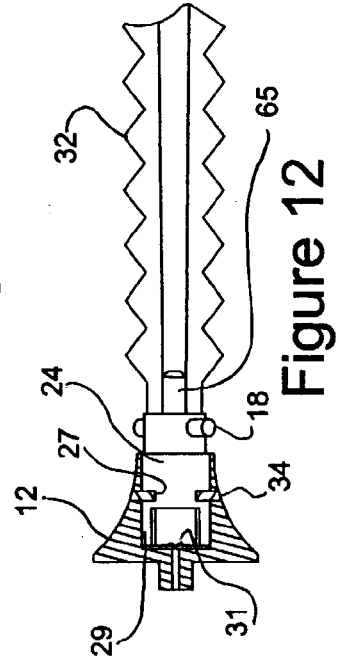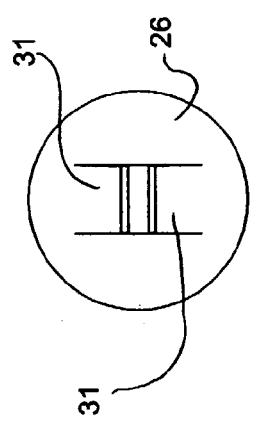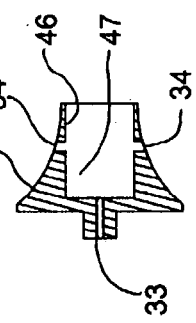

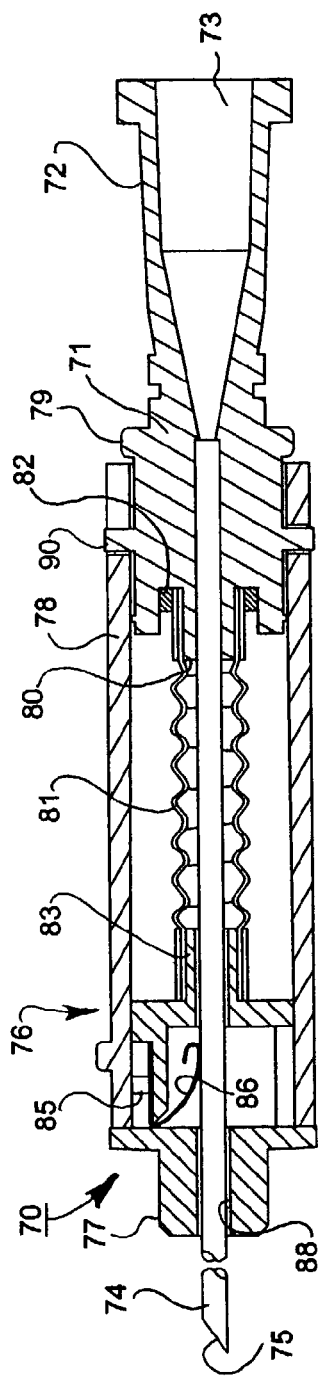
Figure 19
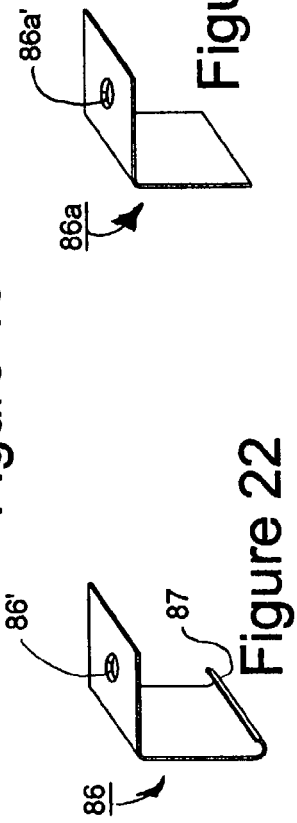
Figure 22
Figure 23
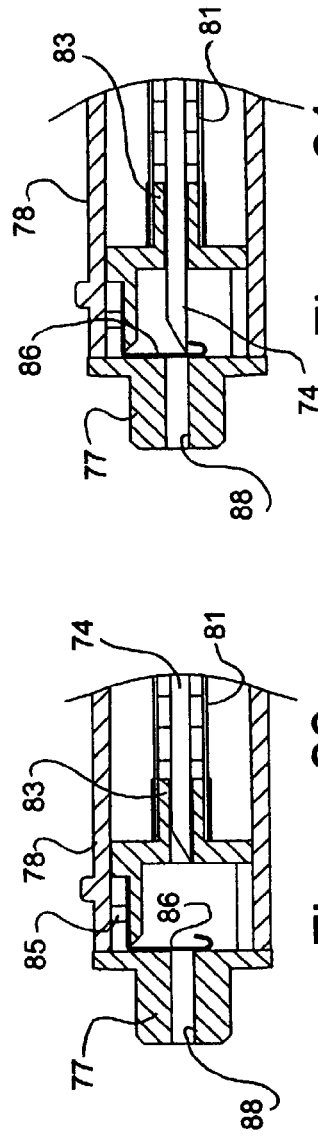
Figure 20
Figure 21

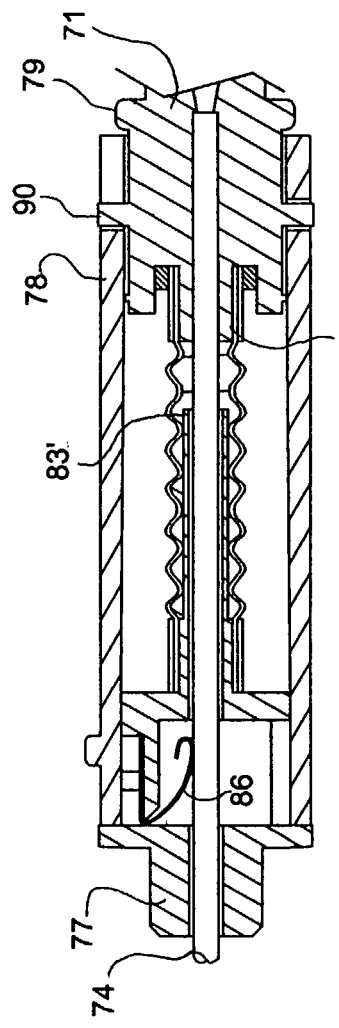
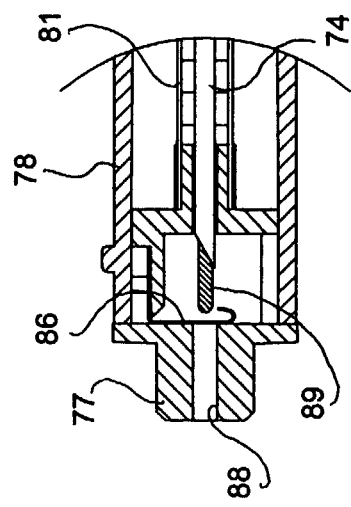
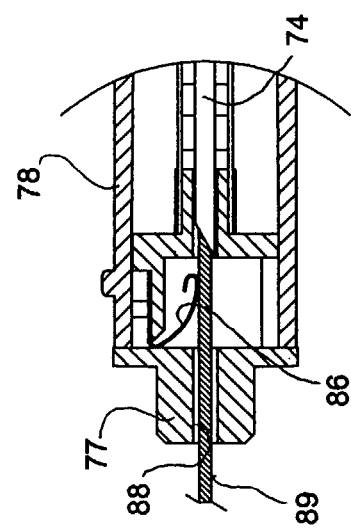
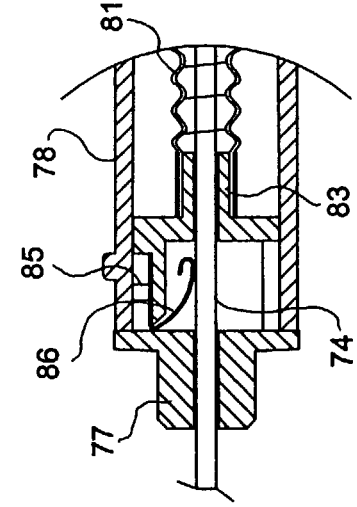

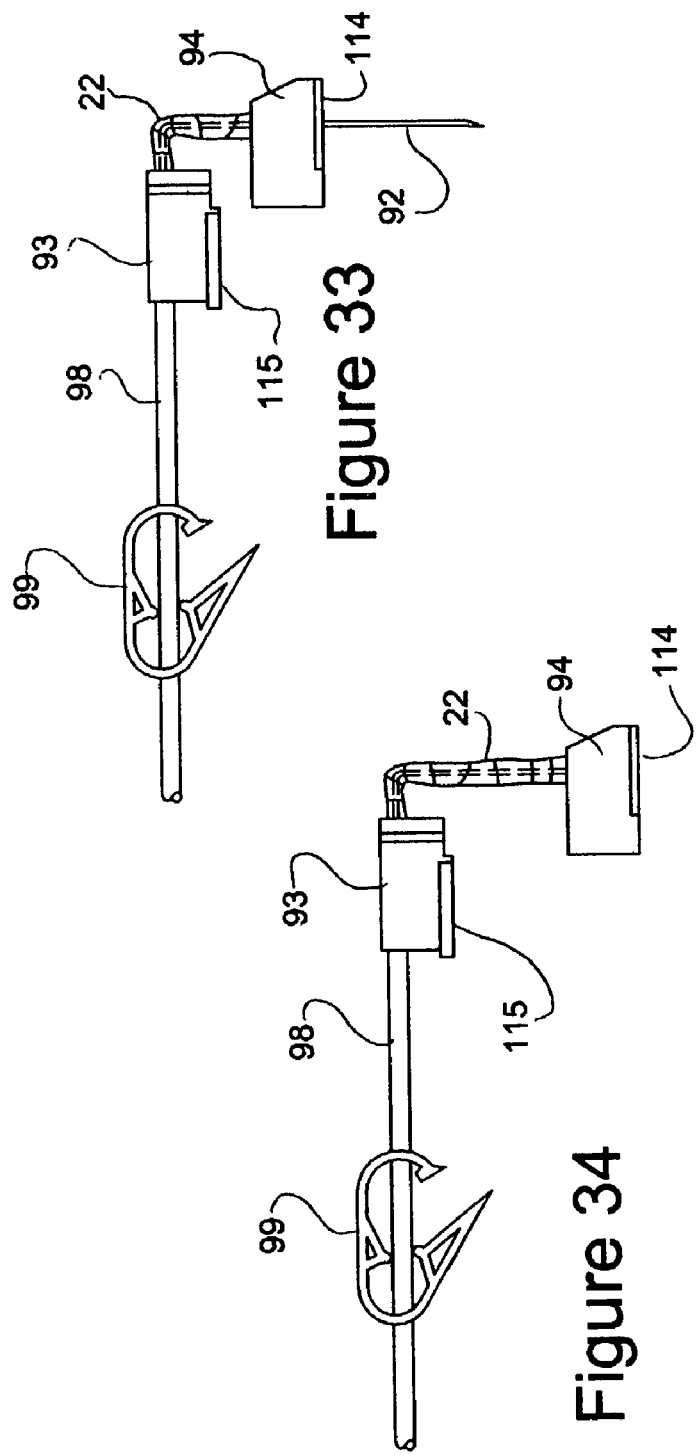
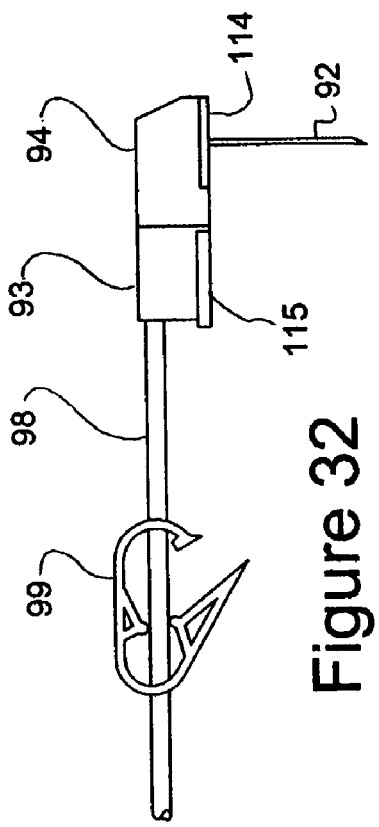

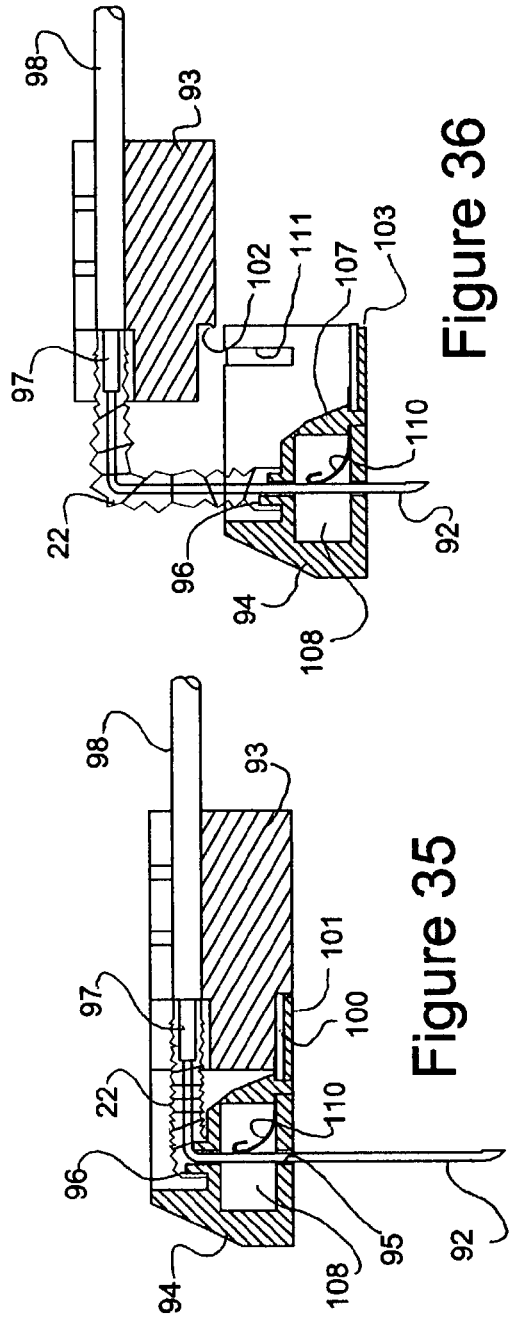
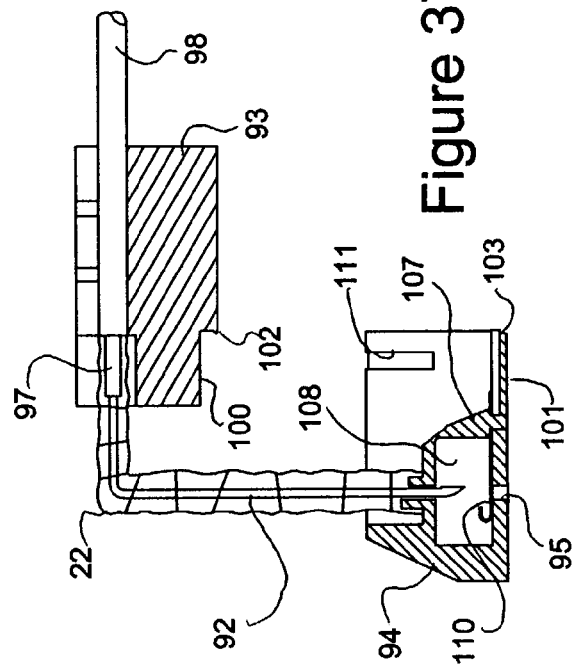

SAFETY NEEDLE WITH COLLAPSIBLE SHEATH

This is application claims priority of Provisional Patent Application No. 60/339,786 filed Dec. 17, 2001.

This invention relates to a safety needle with a collapsible sheath. More particularly, this invention relates to a safety needle that contains a sharpened edge needle that can be rendered harmless to puncture.

Needle protectors are well known and have been in use for many years with needles used with hypodermic syringes. Conventionally, needles are made with hubs and sockets adapted to be attached to the reduced end of a syringe. A molded plastic cap is conventionally removably secured to the hub of the needle. After mounting the needle on the syringe, the cap is removed to expose the needle for use.

Accidental needle stick injuries, unfortunately, are still common in health care workers, such as nurses, physicians, laboratory workers and housekeeping personnel. Needle stick exposures can result in transmission of hepatitis B, as well as acquired immune deficiency syndrome-AIDs, or other transmittable diseases. The health hazards associated with needle stick injuries are of greater risk for health care workers now than ever before.

Accidental needle sticks often occur when a blood drawer attempts to recap a needle after use or leaves a contaminated needle exposed on work surfaces where the blood drawer or other workers accidentally impale themselves.

It is well known that used hypodermic needles are extremely susceptible to transmitting diseases. Hepatitis and other highly contagious diseases can be transmitted by successive use of the same needle by different individuals. In a hospital environment, however, precautions are taken to avoid use of contaminated needles by their expeditious disposal. Problems exist, however, in storing the needle for disposal. Commonly, the protective cap associated with the needle receives the used needle for discarding. However, it is apparent that the bore of the needle cap is dimensioned not much greater than the diameter of the needle and its needle base that removably attaches to a syringe. Misalignment of the needle with respect to the cap when trying to reinsert the needle therein can cause the hand that holds the cap to be punctured, thereby increasing the likelihood to transmission of a contagious disease.

U.S. Pat. Nos. 2,847,995 and 3,134,380 describe shields that are used with hypodermic needles in which the shield or protector is adapted to be accordioned for use and then expanded to cover the tip of the needle. This type of needle tip protector is contemplated to be mounted on the syringe or at least the needle hub and remain in a mounted condition during use. With the rapid increase in AIDS-infected and human carriers, there has been a concentration of providing needle protection. U.S. Pat. No. 4,592,744 describes a specially constructed hub and a self-sheathing assembly. Devices similar to this are known to the art and are utilized to provide a protecting extending flange secured to or as a portion of a tubular cap that is to be reinstalled to cover the needle. Shielded protectors which anticipate flange extensions are numerous and have been promoted and or offered as a protector of the attendant.

Also known are needle tip protectors that anticipate attendant manipulation. Representative of these manipulated devices are those described in U.S. Pat. Nos. 2,876,770; 2,925,083 and 3,306,290. U.S. Pat. No. 4,725267 refers to a corrugated structure having an end cap for enclosing a sharpened needle.

Accordingly, it is an object of this invention to provide a needle assembly with a protective sheath.

It is another object of the invention to reduce the risk of an inadvertent "stick" from used needle.

It is another object of the invention to maintain a used needle in a sealed condition for disposal.

It is another object of this invention to provide a collapsible sheath that corrugates upon collapsing and extends to a tube construction to protect a used needle.

It is another object of this invention to provide a unique positive lock to prevent a sharpened end of a needle from exiting a protective sheath.

It is another object of this invention to provide a positive locking feature for a cap to be disposed over the sharpened end of a needle prior to actuation.

Briefly, the invention is directed to a combination of a housing; a needle extending from the housing; a cap concentrically disposed over the needle and being movable relative to the needle from a first position with the needle extending therethrough to a second position with an end of the needle disposed therein in sealed relation; and a non-resilient tubular sheath of plastic concentrically disposed on and about the needle in a collapsed state and secured to and between the housing and the cap. The sheath is longitudinally extendable from the collapsed state to an extended state in response to movement of the cap from the first position to the second position thereof.

In accordance with the invention, the sheath is characterized in being a film having a high pull force that allows the sheath to be pulled out from the collapsed condition to the extended state without breaking.

The sheath is made of two strips of film material, preferably, polyester, with each strip having a sealable backing, such as polyethylene, thereon facing the other of the strips. The strips are bonded together along two longitudinal edges with the sealable backings in contact to form a tube with two outwardly directed flanges.

In another embodiment of the invention, the cap is made of rigid construction and has a bore for passage of the needle. In addition, a means is disposed in the cap for selectively sealing off the bore to the passage of the needle therethrough. Typically, this means is a spring clip disposed over the bore of cap. In one case, the clip is of a type having a pair of leaves spring-biased onto the needle with the needle in the first position thereof and closing over the bore with the needle in the second position thereof. In another case, the clip has a single leaf spring-biased onto the needle with the needle in the first position thereof and closing over the bore with the needle in the second position thereof.

In this latter embodiment, the sheath is characterized in having a low percentage of elongation to break. This characteristic allows the sheath to be pulled out from the collapsed condition and to be slightly stretched to allow the cap to extend beyond the end of the needle in order to allow the leaf or leaves of the spring clip to slide off the needle into a bore blocking position. Once the clip covers over the bore, the cap is allowed to retract under the force in the stretched sheath.

In still another embodiment, the sheath is particularly adapted to protect a Huber needle after use. In this embodiment, the Huber needle, as is known, has a first leg extending from a housing and a second leg extending perpendicularly of the first leg. The cap is disposed over the second leg of the needle and has a bore through which the second leg extends, for example, for insertion in a subcutaneous medicament delivery device. The cap is movable relative to the second leg from a first position with second leg extending therethrough to a second position with an end of the second leg disposed therein in sealed relation.

In this embodiment, the tubular sheath is concentrically disposed on and about the needle in a collapsed state and is secured to and between the housing and the cap. The sheath, as above, is extendable from the collapsed state to the extended state in response to movement of the cap from the first position to the second position thereof.

In addition, in accordance with the invention, the cap is mounted on the housing in the first position thereof and a means is provided for releaseably locking the cap on the housing. In one case, this means includes a recess in one of the housing and the cap and a projection on the other of the housing and the cap for snap-fitting into the recess. The housing and cap can, thus, be readily handled as a unit to insert the exposed leg of the Huber needle into a subcutaneous delivery device in a patient. In addition, the cap can be readily disengaged from the housing when the needle is removed from the patient.

As above, the cap houses a means, such as a spring clip, for selectively sealing off the bore to the passage of the second leg of the needle after the needle has been used. Also, as above, the spring clip has a leaf biased onto the second leg of the needle with the cap in the first position thereof and closing over the bore with the cap in the second position thereof. The leaf also has a rounded end for sliding on the leg of the needle without scratching of the needle or obstructing movement of the needle.

In this embodiment, the cap is constructed of a plastic material, as by molding, with a plurality of walls to define an interior chamber for sealingly receiving the end of the second leg of the needle in the second position of the cap. In order to gain access to the chamber after molding, for example, to mount the spring clip in place, one of the walls is molded so as to be movable from a first formed position spaced from an other of the walls to allow access to the chamber to a second position in sealed relation to this wall to close the chamber. The spring clip is mounted on this movable wall for movement therewith from the molded first position to the second position. In this way, as the chamber is closed, the spring is put into place.

The cap is also constructed to have a pair of flexible wings extending outwardly from opposite sides of the cap for engaging a body of a patient. A soft pad may also secured to an underside of each wing.

In any of the above embodiments, when the needle is to be removed from a patient or from a subcutaneous device within the patient, the cap is disconnected from the housing and slid along the needle. As the needle is then withdrawn from the patient, the needle enters directly into the cap. During this time, the sheath extends from the collapsed stored position into the extended position. Where a leaf spring is employed within the cap to close over the bore through which the needle is retracted, the cap is pulled beyond the needle thereby stretching the sheath without breaking the sheath until the spring snaps into a blocking position over the bore. The cap is then released so that the sheath retracts slightly into an untensioned state.

The cap covers over the free end of the needle to avoid inadvertent "sticks" from occurring. Further, since the sheath and cap completely envelop the needle, the needle is maintained in a closed sterile condition. Also, any fluids that might be withdrawn with the needle are contained within the sheath and cap. This presupposes that the housing is also closed to prevent a back flow from the needle.

In the case where the sheath is used over a Huber needle, the non-resilient nature of the sheath allows the sheath to be extended from a collapsed position into an extended L-shaped configuraton over the Huber needle.

Since the cap is releasably connected to the housing, the cap and housing can be manipulated as a unit in order to implant the exposed end of the Huber needle in a sub-cutaneous device, such as an infusion port, in a patient. When the needle is to be withdrawn, the cap is held against the patient while the housing is pulled away from the cap. Employing the wings on the cap allows the attendant to keep a firm grip on the cap while the needle is drawn through the cap and the free end of the needle placed within the closed chamber of the cap.

These and other advantages will become more apparent from the following description taken in conjunction with the accompanying drawings wherein:

FIG. 1 illustrates a side view of a syringe assembly constructed in accordance with the invention with a needle in an unprotected position and ready for use;

FIG. 2 illustrates the syringe assembly of FIG. 1 in partial cross section with the slider containing the locking mechanism partially extended along the shank of the needle;

FIG. 3 illustrates the syringe assembly of FIG. 1 in partial cross section with the cap fully extended and enclosing the sharpened point of the needle;

FIG. 4 illustrates sheets of polyester film having a sealable material on one side and cut to size prior to forming;

FIG. 5 illustrates the cap adaptor which is attached to one end of the formed film sheath;

FIG. 6 illustrates the housing adaptor which is attached to the second end of the formed sheath;

FIG. 7 illustrates the housing adaptor and cap adaptor positioned between the two sheets of sealable polyester film with the sealable sides interfacing with each other and the two adaptors;

FIG. 8 illustrates in partial cross section the polyester film sealed to itself with a scalloped edge with a central unsealed tubular section and sealed at the ends to the two adaptors;

FIG. 9 illustrates the "H" clip with the two leaves partially opened;

FIG. 10 illustrates a side view of the "H" clip showing the leaves in a rest condition;

FIG. 11 illustrates in cross section the cap as molded of plastic with openings for the needle and cap adaptor detents;

FIG. 12 illustrates in partial cross section the cap and cap adaptor previously sealed to the; polyester film in place and "H" clip positioned in the distal end of the cap;

FIG. 19 illustrates a cross sectional view of a syringe assembly employing a sheath in accordance with the invention;

FIG. 20 illustrates a position of a leaf spring within the cap of the syringe assembly of FIG. 19 in a blocking position;

FIG. 21 illustrates a view similar to FIG. 20 to indicate the manner in which the spring clip prevents re-emergence of the needle through the cap;

FIG. 22 illustrates a perspective view of the spring of FIGS. 19-21;

FIG. 23 illustrates a perspective view of a modified spring in accordance with the invention;

FIG. 24 illustrates a view similar to FIG. 19 of a modified syringe assembly constructed in accordance with the invention;

FIG. 25 illustrates a partial view of a syringe assembly employing an introducer needled a guide wire in accordance with the invention;

FIG. 26 illustrates a view similar to FIG. 25 with the introducer needle retracted;

FIG. 27 illustrate a view similar to FIGS. 25 and 26 with the introducer needle and guide wire retracted within the cap;

FIG. 32 illustrates a Huber needle constructed in accordance with the invention;

FIG. 33 illustrates a view of the needle of FIG. 32 with a cap and a partially extended state;

FIG. 34 illustrates a view of the needle of FIG. 32 with the cap in a fully extended position;

FIG. 35 illustrates a cross sectional view corresponding to FIG. 32;

FIG. 36 illustrates a cross sectional view of the components of the needle of FIG. 35;

FIG. 37 illustrates a cross sectional view of the component's of the needle of FIG. 35'

Figure 13:
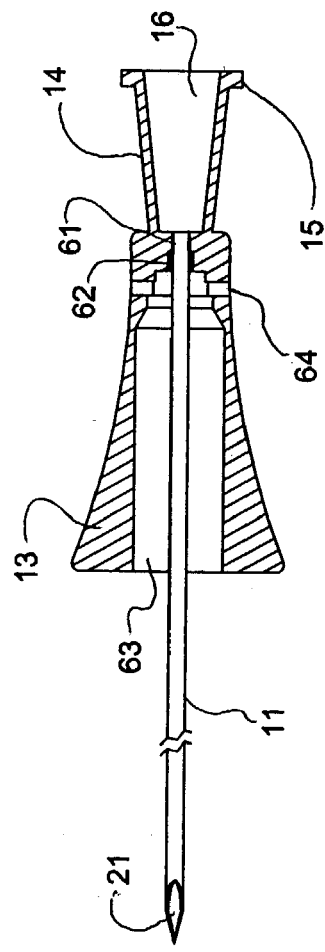
FIG. 13 illustrates in partial cross section the needle positioned within the housing with provision for accepting the housing adaptor detents.

Referring to FIG. 1, the syringe assembly 10 includes a stainless steal needle 11 having a sharpened end 21 that is mounted in a housing 13 in a conventional manner. In addition, the assembly 10 includes a cap 12 that is concentrically disposed over the needle 11 to be moveable relative to the needle from a first position as indicated in FIG. 1 with the needle extending there through to a second position as indicated in FIG. 3 with an end of the needle 11 disposed therein and sealed relation. In addition, as indicated in FIGS. 2 and 3, a non-resilient tubular sheath 22 is concentrically disposed on an about the needle 11 and is secured to and between the housing 13 and cap 12. The sheath 22 is longitudinally extendable from a collapsed state (not shown in FIG. 1) to an extended state as indicated in FIG. 3 in response to movement of the cap 12 from the first position to the second position thereof.

Both the cap 12 and housing 13 are made of suitable materials, such as a plastic, and each is of rigid construction. In addition, means is provided for selectively locking the cap 12 on the housing 13. As indicated in FIGS. 1 and 2, this means is formed as a bayonet-type lock. That is to say, the housing 13 is provided with a pair of oppositely disposed L-shaped slots 19 (only one of which is shown) in an end of the housing 13 while a pair of pins 18 are formed inegral with the cap 12 for sliding within each respective slot 19. Upon assembly, the pin 18 is slid into the slot 19 through the short leg, as viewed, and rotated into the long leg, as shown, to achieve a positive lock.

The proximal portion of the housing 14 includes a female luer hub 14 having a sealing thread 15 for connection to a syringe, extension set or the like (not shown).

When used, after the neddle 11 has been inserted into a patient for whatever reason and is to be withdrawn, the cap 12 is rotated relative to the housing 13 so as to align the pins 18 with the respective short legs of the respective slots 19. There after, the cap 12 is moved manually along the length of the needle 11 to a point where the needle emerges from the body of the patent. As indicated in FIG. 2, as the cap 12 moves away from the housing 13, the sheath 22 begins to play-out from the housing 13. As the needle 11 emerges from the body of the patent, the needle 11 moves directly into the cap 12. At this time, as indicated in FIG. 3, the sheath 22 is fully extended.

The sheath 22 is characterized in having a high tensile strength that allows the sheath 22 to be pulled out from the collapsed condition of FIG. 1 to the extended state of FIG. 3 without breaking.

Referring to FIG. 4, the sheath is made of two strips 23 of film material. Each strip 23 is made, preferably, of a polyester, such as Mylar, with a co-extruded sealable backing 23' of a polyethylene, such as Surlyn, facing the other of the strips 23. The strips 23 are bonded together along two longitudinal edges with the sealable backings 23' in contact to form a tube with two outwardly directed flanges. The strips are characterised in being made of 92 ga. Mylar LB having an ultimate tensile strength of, at a minimum, 27 psi as tested in accordance with ASTM D882 and an ultimate elongation of, at most, 80% in accordance with ASTM D882.

The polyester film may be 0.5 to 1.0 mil thick while the backing 23' maybe a polyethylene film of from 0.5 to 2.0 mils thick. Alternatively, a commercially available adhesive may be used as a backing.

Referring to FIGS. 5 and 7, in order to mount the sheath 22 in the syringe assembly of FIG. 1, one end of the sheath 22 is secured to a cap adapter 24 while the other end is secured to a housing adapter 25.

Figure 18:
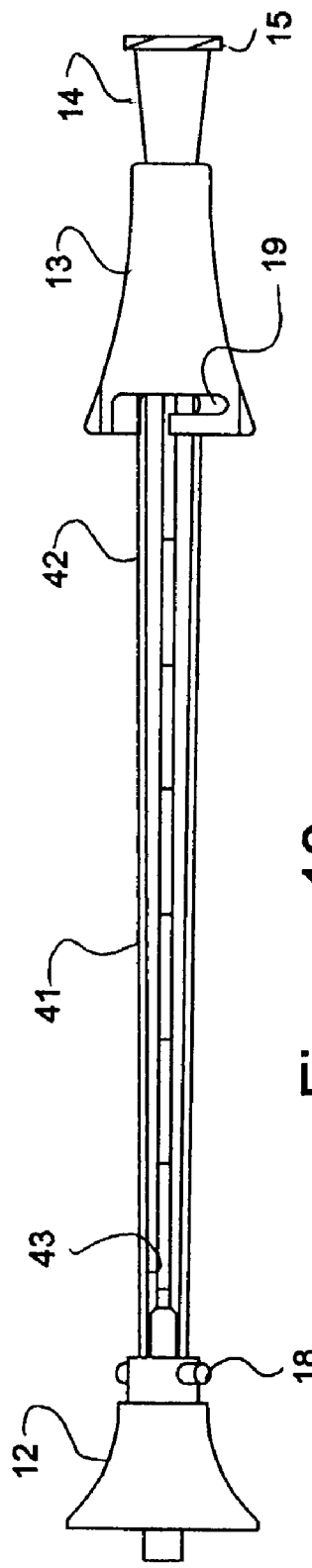
FIG. 18 illustrates another embodiment of the invention in partial cross section in which the corrugated sheath is formed in the shape of a conical shaped tube with fins.

The strips of film 23 are of unitary construction and are sealed together using suitable ultrasonic sealing techniques. For example, the two sheets 23 may be placed in a die having the desired configuration with the sealing surfaces facing one another. The adapters 24, 25 are placed at opposite ends of the die and positioned between the two sealable portions 23 of the strips 23. A suitable cutting/sealing die is then used to seal the two films together including sealing the adapters 24, 25 to the films 23. The cutting die which normally is an integral part of the process may scallop the edges of the film as indicated in FIG. 3 or cut the film tubular geometry as indicated in FIG. 18. In either event, the interior wall of the sheath 22 has a smaller equivalent diameter at the distal and 35 and a larger equivalent diameter 36 at the proximal end.

Depending upon the angle which these two diameters 35, 36 create for a given film thickness, the result called the "compression ratio" determines the length the formed sheath 22 can be expanded for a given initial compressed length. For example, for a 0.5 mil polyester film having a 1.5 mil backing of polyethylene and initial equivalent diameter of 0.045 inch and 0.060 inch, a 1.0 inch length of compressed sheath 22 will expand to 7 inches in free length. This property provides for a substantial free length only a minimum amount of storage length. Compression ratios at relatively low variances between equivalent diameters at the distal and proximal ends result in "compression ratios" of 10 to 15. An important feature is that the sheath 22 has a small outer diameter with a compression ratio of 10 or more. The result is a low profile compact sheath which can be extended to significant lengths and that exhibits a high tensile strength. For example, a sheath 22 made of 1.0 mil polyester films 23 with an apparent diameter of 0.050 inches has a breaking force of 17 pounds.

Referring to FIGS. 5 and 7, the cap adapter 24 has a hollow tubular projection 65 for sealing to the sheath 22. In addition, the cap adapter 24 has a pair of outwardly directed detents 27 and a pair of longitudinal extensions 29 for purposes as described below.

Referring to FIGS. 6 and 7, the housing adapter 25 has a hollow tubular projection 66 for securement to the sheath 22 as well as outwardly directed spring detents 28 for purposes as explained below.

Referring to FIG. 11, the cap 12 is made of molded plastic and has a pair of side apertures 34 on opposite sides for receiving the detents 27 of the cap adapter 24 as indicated in FIG. 12. The cap 12 also has a central hub with a central bore 33 to allow passage of a needle 11 (see FIG. 1).

Referring to FIG. 12, a means in the form of a spring clip 26 is disposed within the cap 12 and is fitted within a central bore 46 of the cap 12 against a vertical wall 47 as indicated in FIGS. 9 and 10. The clip 26 is in the form of an "H" clip having a pair of spring-biased leaves 31 directed outwardly of a central opening.

Referring to FIG. 12, the cap adapter 24 is fitted into the cap 12 so that the detents 27 of the adapter 24 snap into the appetures 34 the cap. At the same time, the extensions 29 on the end of the adapter 24 abut against the spring clip 26 to retain the clip 26 in place. The position of the detents 27 as related to the position of the pins 18 so that when the detents 27 snap into place, the pins 18 are oriented relative to the slots 19 in the housing 13 (see FIG. 1).

The spring clip 26 is preferably made of stainless steel with a thickness of 5 mils and an H configuration is punched out of the clip so that the two leaves 31 have a small opening therebetween. This opening is sufficient to reduce the frictional resistance on a needle 11 positioned between the leaves so that the cap 12 is able to move freely over the needle 11. Upon retraction of the needle 11 into the cap 12, the leaves 31 close to the position indicated in FIG. 10. This closure is sufficient to prevent the sharp point 21 of the needle 11 from penetrating the clip 26 thereby preventing the needle 11 from reemerging from the cap 12.

The sheath 22 is characterized in having low percentage of elongation to break, for example, no more than 80 percent. This characteristic allows the sheath 22 to be pulled out from the, collapsed condition of FIG. 1 and to be sloghtly stretched to allow the cap 12 to extend beyond the end 21 of the needle 11 in order to allow the leaves 31 of the spring clip 26 to slide off the needle 11 into a bore locking position. Once the clip leaves 31 cover over the bore 33, the cap 12 is allowed to retract under the force of the stretched sheet 22. With the needle point 21 within the cap 12 and beyond the clip 26, further movement of the cap 12 either proximally or distally is prevented. The sharp tip 21 of the needle 11 is thus trapped within the cap 12. The safety needle may now be safely discarded.

Referring to FIG. 13, the needle 11 is fitted into a bore 61 of the housing 13 and secured in place by a suitable adhesive 62. The needle 11 is aligned with a tapered bore 16 of the female luer lock hub 14 that provides a means for attaching the housing 13 to a male luer adapter (not shown) to secure a connection, for example, to a syringe.

Figure 14:
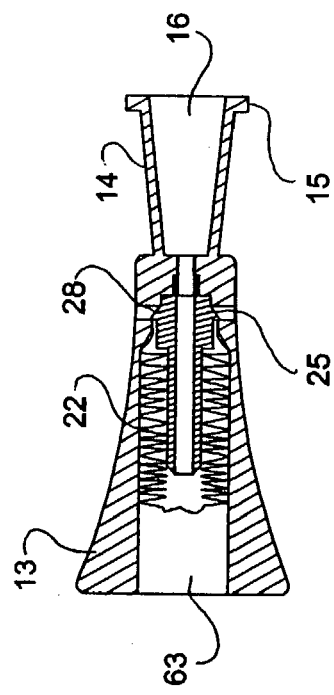
FIG. 14 illustrates in cross section the housing adaptor locked within the needle holder housing and attached plastic film collapsed therein.

The housing 13 also has a central opening 63 for receiving the housing adapter 25 of the cap 12 as indicated in FIG. 14. To this end, a pair of openings 64 are provided in the housing 13 in order to receive detents 28 of the housing adapter 25 as indicated in FIG. 14.

Referring to FIG. 14, when the cap 12 (not shown) is mounted on the housing 13, the housing adapter 25 is forced under pressure into the central opening 63 of the housing 13 until the detents 28 which compress slightly during movement through the central opening 63 are aligned with the openings 64. At this point, the detents 28 expand to fill the openings 64. A lock between the housing 13 and housing adapter 25 is thus achieved thereby securing the attached sheath 22 to the housing 13., via the adapter 25. As illustrated, the sheath 22 is disposed in a compressed or corrugated condition within the central opening 63. The needle 11 is omitted from FIG. 14 for purposes of clarity.

Figure 15:
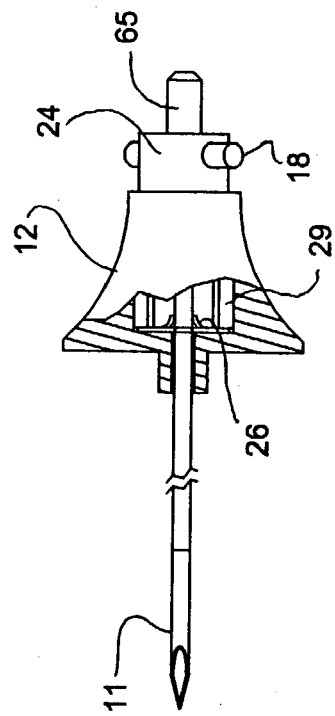
FIG. 15 illustrates in partial cross section the "H" clip secured in place by the cap adaptor extension.

Referring to FIG. 15, when the cap 12 is mounted in place, the needle 11 passes through the spring clip 26 with the leaves flexed outwardly in order to slide along the needle 11 when the cap 12 is to be extended.

Figure 16:
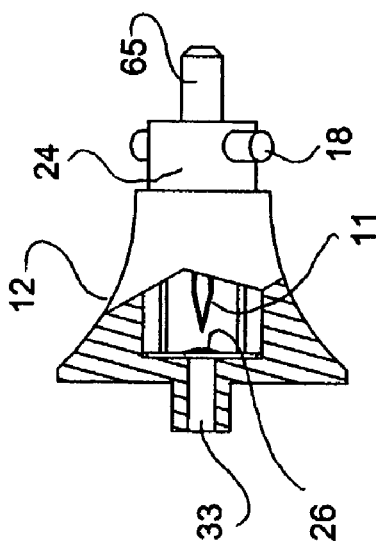
FIG. 16 illustrates in partial cross section the "H" clip retracted after the needle is moved into the cap.

Referring to FIG. 16, when the cap 12 is extended beyond the sharpened end of the needle, the leaves of the spring clip 26 flex inwardly thereby blocking the bore 33 to prevent re-emergence of the needle through the bore 33.

Figure 17:
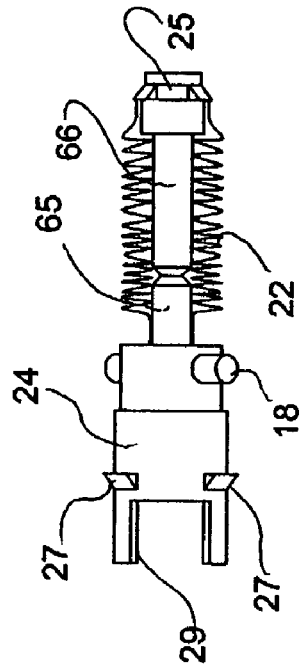
FIG. 17 illustrates the cap adaptor, housing adaptor and sealed film as an assembly unit prior to placement in the housing and cap.

Referring to FIG. 17, the adapters 24, 25 and sheath 22 form an assembly that can be handled as a unit. In the condition illustrated, the tubular extensions 65, 66 of the adapters 24, 25 are abutted together and the sheath 22 is collapsed within the space between the adapters 24, 25. This assembly is placed over the needle 11 and slid into the housing 13 for securement in place as indicated in FIG. 14. At this time, the cap 12 is aligned with the needle 11. A blunt cannula (not shown) is then placed through the cap 12 from the distal position and the clip 26 is moved over the blunt cannula to open up the leaves 26. The needle 11 is then placed within the blunt cannula which is now removed so that the needle 11 is now within the clip 26 and the cap 12 can now be moved along the needle 11 towards the housing 13. The cap 12 is moved along the needle 11 until contacting the adapter extensions 29 which tend to align the clip 26 perpendicular to the axis of the needle 11. The cap 12 is then forced into the housing 13 so that the detents 27, 28 previously oriented during formation of the sheath 22 are compressed. When the respective detents 27, 28 snap into the respective openings 34, 64, the adapters 24, 25 are locked within the respective cap 12 and housing 13. At the same time, the pins 18 of the cap 12 enter into the recesses 19 of the housing 13. A turning of the cap 12, for example counterclockwise approximately 45 degrees secures the cap 12 within the housing 13.

In use, the cap (not shown) which ordinarily protects the sharpened end 21 of the needle 11 from damage during storage is removed thereby exposing the assembly as shown in FIG. 1. This assembly may or may not be attached to a syringe, guide wire or the like part to use. The needle 11 now penetrates a patient's skin and normally interdicts a blood vessel. After infusion, guide wire placement, or the like, the needle may be withdrawn from the patient. In one instruction for use, the cap 12 at that time is rotated counterclockwise to release the cap 12 from the housing 17. The cap 12 is then moved to an extended position and as the needle is removed from the patient the cap 12 entraps the sharp end 21 of the needle. In this position, the assembly may be disposed of without concern for a needle stick.

Referring to FIG. 18, wherein like reference characters indicate like parts as above, the sheath 41 may be formed in a tapered or conical shape with tapered or conical outer and inner walls 42, 43.

Referring to FIG. 19, the syringe assembly 70 includes a housing 71 having a female luer hub 72 at one end that defines a flash chamber 73. As above, a needle 74 with a sharp end 75 is mounted in the housing 71 in fixed manner to communicate with the flash chamber 73.

The syringe assembly 70 also has a cap 76 slidably mounted on the housing 71. In this embodiment, the cap 76 has a head 77 concentrically disposed over the needle 74 and an elongated sleeve 78 that extends from the head 77 over the housing 71. The head 77 and sleeve 78 are secured together in any suitable manner, such as by bonding or ultrasonic welding.

As shown, the sleeve 78 abuts against an annular flange 79 on the housing 71 so as to be located in a retracted position.

The housing 71 has a tubular extension 80 on which one end of a sheath 81 of a material as described above is mounted in concentric manner. As indicated, a suitable adhesive 82 is provided to sealingly secure the end of the sheath 81 to the housing 71 about the tubular extension 80.

The opposite end of the sheath 81 is mounted on a tubular extension 83 of the head 77 by means of a suitable adhesive or other suitable sealing technique. This head 77 is sized to be slidably received within the sleeve 78. In addition, the head 77 has a radially outwardly directed post 85 over which a spring clip 86 is mounted.

As indicated in FIG. 22, the spring clip 86 has a bore 86' for passage of the post 85 and is of L-shape with a leaf having a rounded end 87 for resting against the needle 74 as indicated if FIG. 19.

The head 77 has a central bore 88 through which the needle 74 passes. In addition, the leaf of the spring clip 86 is sized to lay over the bore 88 in order to prevent re-emergence of the needle 74 therethrough as described below.

Referring to FIG. 23, the spring clip 86a may be formed without a rounded end as indicated and with a bore 86a'.

In order to assemble the syringe assembly 70, the sheath 81 is mounted on the tubular extension 83 of the head 77. The spring clip 86 is then mounted on the post 85 located on the head 77. The head 77 is then inserted into the sleeve 78 and bonded in place.

Next, the needle 74 is inserted into the head 77 through the central bore 88 and through the sheath 81 into the housing 71. The needle 74 is then bonded or otherwise secured to the housing 71.

Thereafter, the sheath 81 is bonded to the extension 80 of the housing 71.

Figure 30:
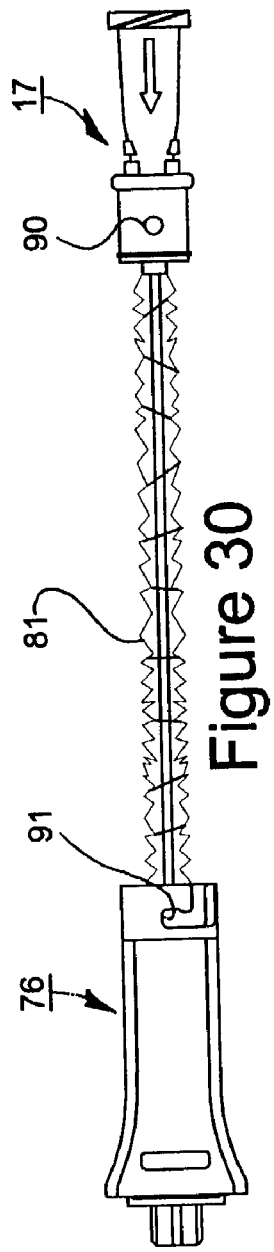
FIG. 30 illustrates the syringe assembly of FIG. 28 with the cap in a fully extended position.

The sleeve 78 is then slid onto the housing 71 into abutment with the annular flange 79. As indicated in FIG. 30, the housing 71 is provided with a post 90 to be fitted into an L-shaped slot 91 in the cap 76 to form a bayonet conection to secure the cap 76 to the housing 71.

In use, when the needle 74 is being withdrawn from a patient, the cap 76 is slid off the housing 71 and moved over the needle 74. As the sharp end 75 of the needle is withdrawn from the patient the cap 76 is moved beyond the end 75 of the needle as indicated in FIG. 20 wherein like reference charac- ters indicate like parts as above. At this time, the leaf of the spring clip 86 snaps forwardly to cover over the bore 88 in the head 77.

Referring to FIG. 21, should the needle 74 be moved forward, the spring clip 86 prevents reemergence of the needle 74 through the bore 88 of the head 77 of the cap 76.

Referring to FIG. 24, wherein like reference characters indicate like parts as above, the head 77 may be modified to have an elongated tubular projection 83' to allow the needle 74 to move forward and to retract without contacting the sheath 81 and thereby avoid any friction contact of the needle 74 with the sheath 81.

Referring FIGS. 25, 26 and 27, wherein like reference characters indicate like parts as above, the needle 74' may be an introducer needle which cooperates with a guide wire 89 (see FIG. 26). In this embodiment, the introducer needle 74 is first retracted from a patient from a position indicated in FIG. 25 to the position indicated in FIG. 26. Thereafter, the guide wire 89 is retracted from the patient and moved into the cap 76 a sufficient extent to permit the leaf spring 85 to snap back over the bore 88 as indicated in FIG. 27 thereby blocking re-emergence of the introducer needle 74' or guide wire 89.

Figure 29:
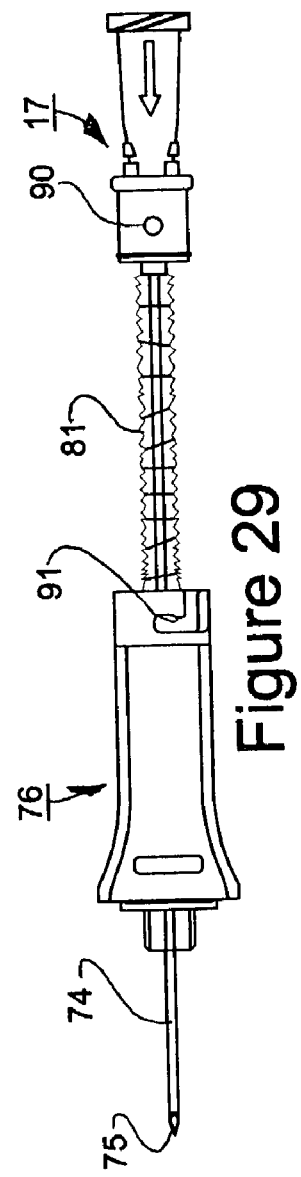
FIG. 29 illustrates a view of the syringe assembly of FIG. 28 with the cap in a partially extended state.
Figure 28:
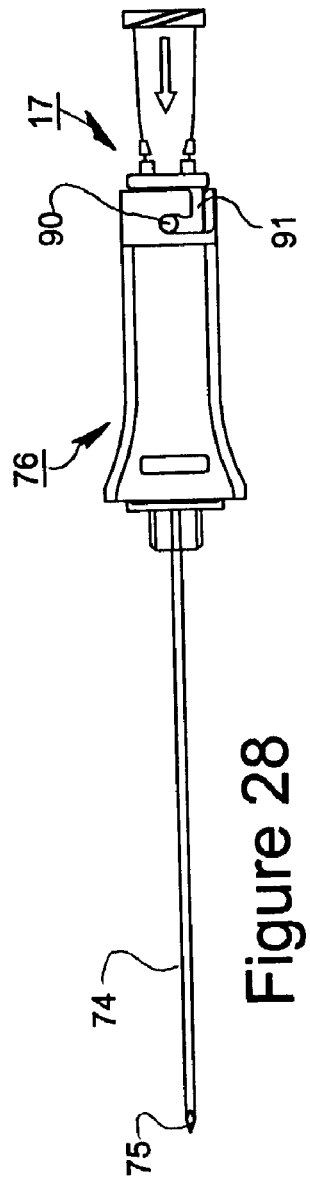
FIG. 28 illustrates a top view of the syringe assembly of FIG. 19.

Referring to FIGS. 28, 29 and 30 wherein like reference characters indicate like parts as above, the cap 76 may be mounted on the housing 71 using a bayonet lock connection similar to that as described above. In this embodiment, the housing 71 is provided with a pair of posts 90 (only one of which is shown) while the sleeve 78 of the cap has a pair of L-shaped groves 91 each of which is positioned to receive a post 90 of the housing 71. In order to release the cap 76, the cap 76 is rotated from the position shown in FIG. 28 to the position shown in FIG. 29 and pulled axially from the housing 71. The cap 76 is then extended to the fully extended position of the sheath 81 (FIG. 30) so as to close over the end 75 of the needle 74.

Figure 31:
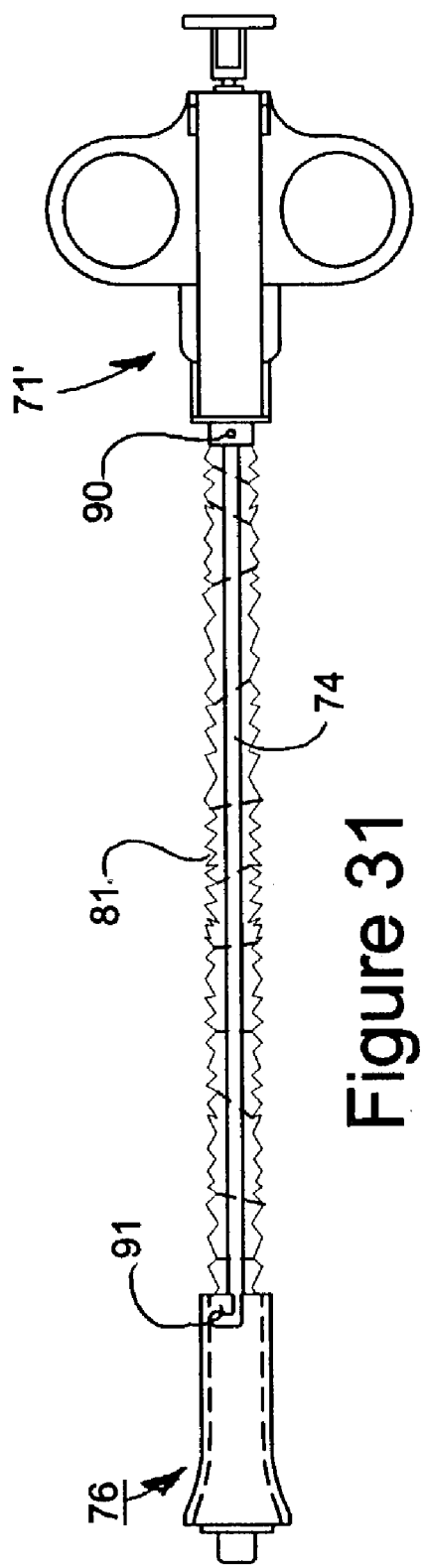
FIG. 31 illustrates a view of a biopsy needle assembly constructed in accordance with the invention.

Referring to FIG. 31, wherein like reference characters indicate like parts as above, the needle assembly may be constructed as a biopsy needle. In this case, the housing 71' is constructed in a conventional manner and need not be further described.

Referring to FIGS. 32, 33 and 34, wherein like reference characters indicate like parts as above, the sheath 22 is particularly useful for a Huber needle 92. In this embodiment, the sheath 22 extends between a housing 93 and a cap 94.

Referring to FIG. 35, the Huber needle 92 is of L-shaped construction and has a proximal leg secured in a fixed manner within the housing 93. The second leg of the needle 92 extends through the cap 94.

Figure 38:
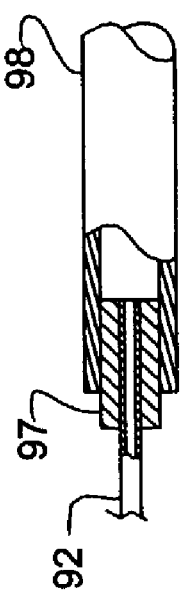
FIG. 38 illustrates a enlarged view of a connection of the Huber needle in the housing of the needle assembly of FIG. 32.

The cap 94 is of generally block construction and is slide- able along the leg of the needle 92 from a position as indicated in FIG. 32 to a position as indicated in FIG. 34. The cap 94 includes a bore 95 for passage of the needle 92 and is move- able from the position shown in FIG. 35 to the position shown in FIG. 37. The cap 94 includes a tubular extension 96 on which the sheath 22 is secured in a manner as described above. Likewise, as shown in FIGS. 35 and 38, the opposite end of the sheath 22 is secured to a tubular bushing 97 (e.g. of polyvinylchloride) that extends from a line 98 (e.g. of poly- vinylchloride) mounted in the housing 93. As indicated, the tubular bushing 97 mounts the needle 92 and communicates the needle 92 with the line 98. As indicated in FIG. 32, a clip 99 may be disposed on the line 98 in order to control a flow of fluid therethrough.

Figure 39:
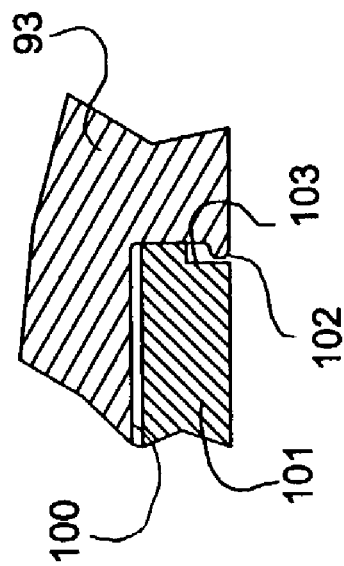
FIG. 39 illustrates a cross sectional view of a snap fit connection of the cap and housing of the Huber assembly of FIG. 32.

Referring to FIGS. 35 and 39, the cap 94 and housing 93 are constructed so that the cap 94 is fitted into the housing 93 in a snap-fit manner to be handled as a unit. To this end, the housing 93 has a recess 100 while the cap 94 has an extension 101 that fits into the recess 100. In addition, as indicated in FIG. 39, a small shoulder 102 is provided at the mouth of the recess 100 of the housing 93 while the extension 101 of the cap has a small recess 103 to receive the projection 102. In this respect, when the extension 101 of the cap 94 is fitted into the recess 100 of the housing 93, the extension 101 snaps past the projection 102 and is thus held in place in a snap fit manner. In order to disconnect the cap 94 from the housing 93, the housing 93 and the cap 94 are each manually grasped and moved apart.

Figure 40:
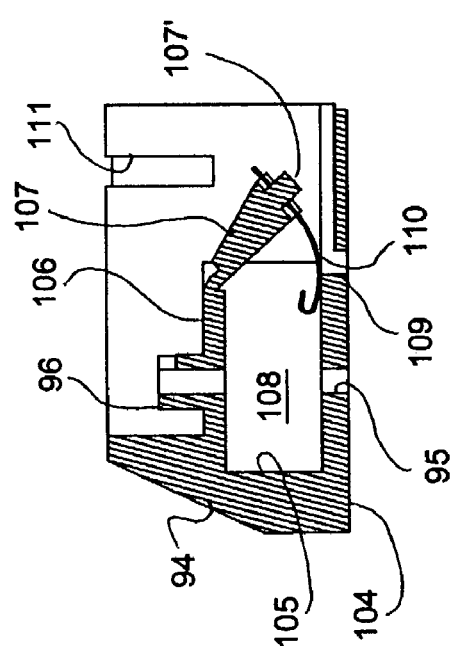
FIG. 40 illustrates a cross sectional view of the cap of the assembly of FIG. 37 prior to final assembly.

Referring to FIG. 40, the cap 94 is made of a plastic material and is initially molded with a plurality of walls 104, 105, 106, 107 to define a chamber 108. As indicated, one of the walls 107 is movable from a first formed position spaced from the bottom wall 108 to a second perpendicular position in sealed relation to the bottom wall 104 in order to close the chamber 108. In this respect, the movable wall 107 has a reduced end 107' that is able to snap into a slot 109 in the fixed bottom wall 104.

As shown in FIG. 40, the movable wall 107 carries a spring clip 110 that is sized to extend over the bore 95 in the bottom wall 104 when the movable wall 107 is brought into a closed position (FIG. 37).

Allowing the wall 107 to be moved permits mounting of the spring clip 110 in place in an otherwise closed chamber 108.

Referring to FIG. 37, the cap 94 is provided with a pair of tracks (grooves) 111 on opposite sides to receive corresponding rails (not shown) or projecting ears (not shown) of the housing 93.

Figure 42:
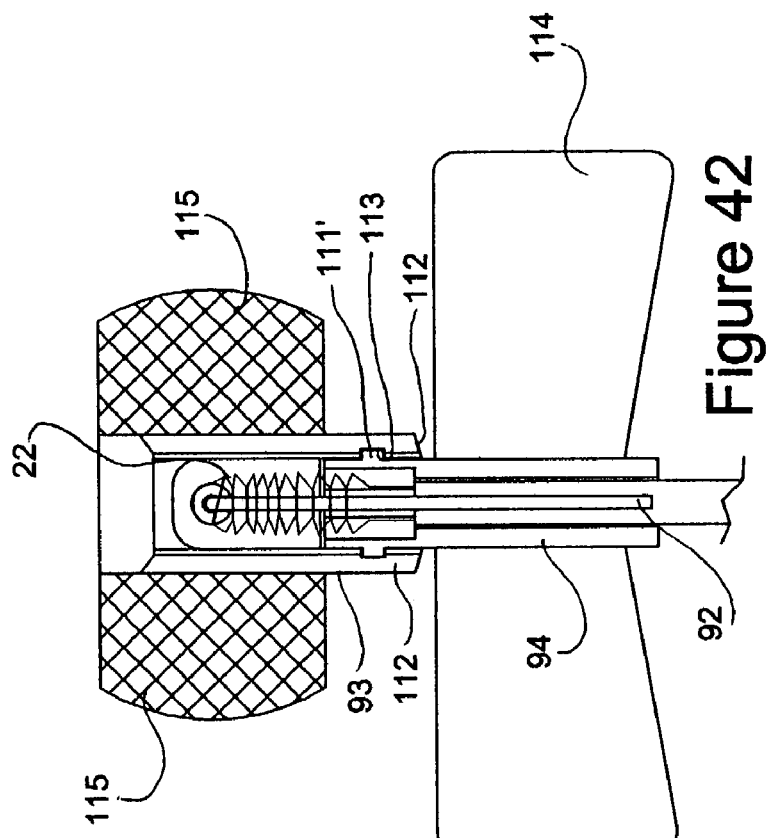
FIG. 42 illustrates a top view of the Huber needle assembly of FIG. 40.
Figure 41:
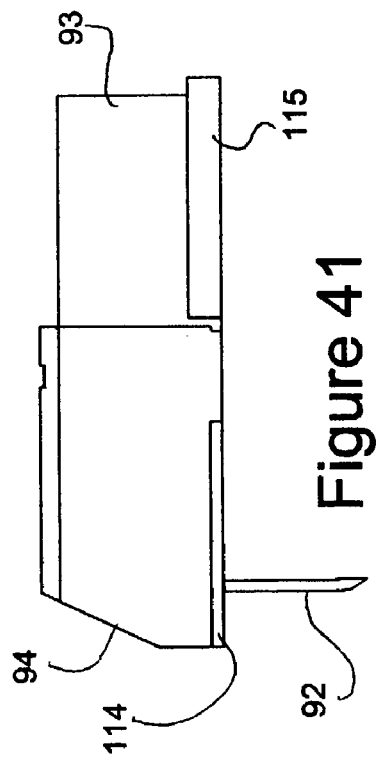
FIG. 41 illustrates a side view of a modified Huber needle assembly with accordance with the invention.

Referring to FIGS. 41 and 42, wherein like reference characters indicate like parts as above, the cap 94 maybe formed as a slender body in order to slide between two ears 112 of the housing 93. In addition, the alignment tracks 111' may be placed in the ears 112 while the cooperating rails 113 are placed on the cap 94. In addition, the underside of the cap 94 is provided with a pair of outwardly directed wings 114 of flexible material and the underside of the housing 93 is provided with a pair of outwardly directed wings 115.

Figure 43:
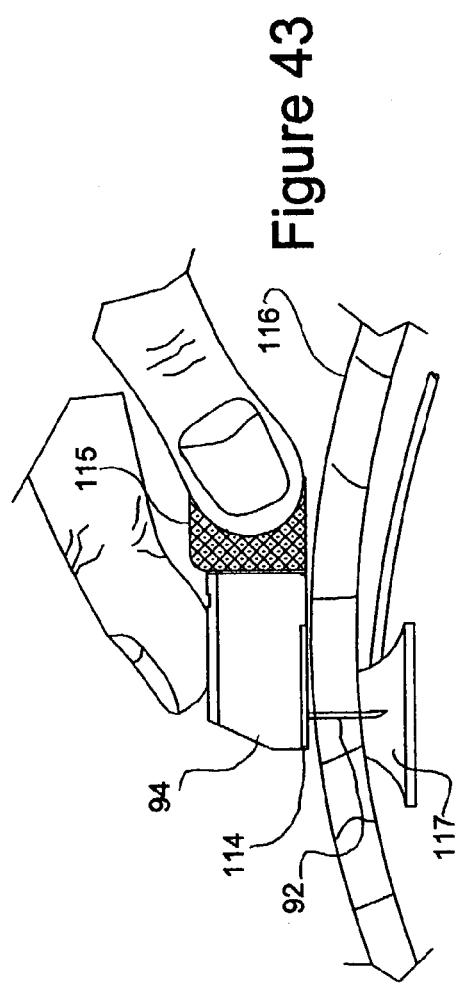
FIG. 43 illustrates a manner of inserting a Huber needle assembly of FIG. 40 in a patient.

In order to use the Huber needle assembly, the housing 93 and cap 94 are manipulated as indicated in FIG. 43 so that the exposed end of the needle 92 is able to pierce through the sub-cutaneous tissue 116 of a patient into a mendicament delivery device, such as an infusion port 117, below the tissue 116. The cap 94 is particularly useful in allowing finger pressure to be applied to push the needle 92 into the port 117.

Figure 44:
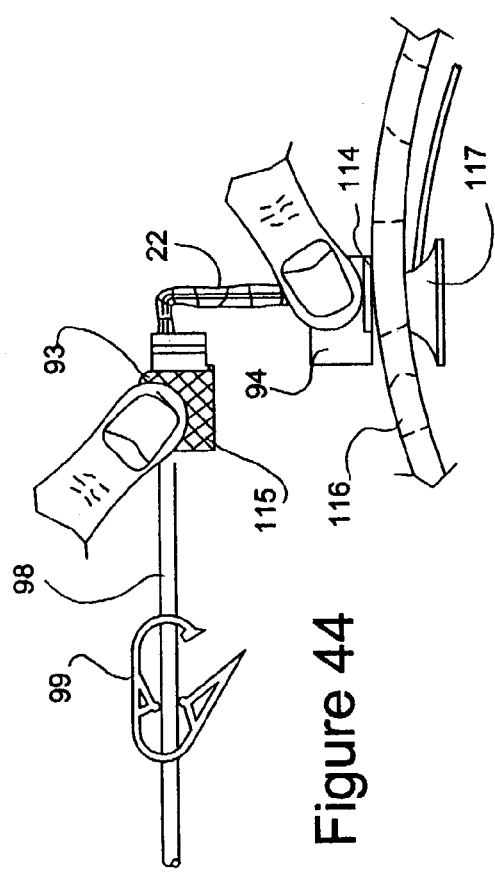
FIG. 44 illustrates a view of the Huber needle assembly of FIG. 32 during removal from an infusion port in a patient.

Referring to FIG. 44, when it is desired to remove the Huber needle 92, the wings 114 on the cap 94 which lay against the tissue 116 are pressed against the patient to hold the cap 94 in place. Thereafter, the housing 93 is lifted way from the cap 94 thereby pulling the needle 92 out of the infusion port 117 and out of the patient. During this time, the sheath 22 is extended from the collapsed state to the extended state.

Due to the flexible nature of the sheath 22, the sheath 22 is readily pulled out of the housing 93 as indicated in FIG. 36 and extended into the fully extended state as indicated in FIGS. 37 and 44 without tearing or impeding movement of the housing 93 away from the cap 94. Once the needle 92 has moved into the position indicated in FIG. 37 the spring clip 110 snaps over the bore 95 in the cap 94 to prevent reemergence of the needle 92. Further, since the chamber 108 within the cap 94 is closed, the end of the needle 92 is maintained in a sealed closed sterile manner. As this time, the Huber needle assembly may be discarded with the needle 92 contained in a protective manner.

The invention thus provides a simple construction for entrapping a needle after use in order to protect against inadvertent "sticks". The use of a fleaxible tubular sheath to encase the needle along with the cap that is attached to the sheath allows the sharp end of various types of needle to be trapped within a sealed chamber. Where the sheath is made of a transparent material, the encased needle may be readily seen to determine if the needle is broken or not.

Further, the invention provides a relatively simple structure that can be used to entrap the sharp end of a Huber needle after use.

The invention also provides a positive locking feature for a cap to be disposed over the sharpened end of a needle prior to actuation as well as a unique positive lock to prevent a sharpened of a needle from exiting a protective sheath.

What is claimed is:

1. In combination,
a housing;
a needle extending from said housing;
a cap concentrically disposed over said needle and having a bore for passage of said needle therethrough, said cap being movable relative to said needle from a first position with said needle extending through said bore to a second position with an end of said needle disposed therein in spaced relation to said bore and in sealed relation; and
a non-resilient tubular sheath of plastic film concentrically disposed on and about said needle in a collapsed state and secured to and between said housing and said cap, said sheath being longitudinally extendable from said collapsed state to an extended state in response to movement of said cap from said first position to said second position thereof and being in a stretched condition with said end of said needle withdrawn from said bore to maintain said cap in sealed relation to said needle and being characterized in having a low percentage of elongation to break and a high tensile strength.

2. The combination as set forth in claim 1 wherein said sheath has a percentage of elongation of at most 80%.

3. The combination as set forth in claim 1 wherein said sheath has a tensile strength of at least 27 psi.

4. The combination as set forth in claim 1 wherein said sheath is made of polyester film material.

5. The combination as set forth in claim 1 wherein said sheath is made of two strips of film material, each said strip having a sealable backing thereon facing the other of said strips, said strips being bonded together along two longitudinal edges thereof.

6. The combination as set forth in claim 1 wherein said cap is of rigid material.

7. The combination as set forth in claim 1 wherein said needle end abuts said cap with said sheath in said stretched condition.

8. In combination,
a housing;
a needle extending from said housing;
a rigid cap concentrically disposed over said needle and having a bore for passage of said needle therethrough, said cap being movable relative to said needle from a first position with said needle extending through said bore to a second position with an end of said needle disposed therein in spaced relation to said bore;
means disposed in said cap for selectively sealing off said bore to the passage of said needle therethrough; and
a tubular sheath concentrically disposed on and about said needle in a collapsed state and secured to and between said housing and said cap, said sheath being longitudinally extendable from said collapsed state to an extended state in response to movement of said cap from said first position to said second position thereof.

9. The combination as set forth in claim 8 wherein said cap is mounted on said housing in said first position thereof.

10. The combination as set forth in claim 9 further comprising means for selectively locking said cap on said housing.

11. The combination as set forth in claim 10 wherein said means includes at least one L-shaped slot in an end of said housing and a pin on and projecting from said cap, said pin being slidably received in said slot.

12. The combination as set forth In claim 9 wherein said means is a spring clip disposed over said bore of said cap, said clip having a pair of leaves spring biased onto said needle with said needle in said first position thereof and closing over said bore with said needle in said second position thereof.

13. The combination as set forth in claim 9 wherein said means is a spring clip disposed over said bore of said cap, said clip having a leaf spring biased onto said needle with said needle in said first position thereof and closing over said bore with said needle in said second position thereof.

\* \* \* \* \*